United States Patent [19]

Del Mar

[11] Patent Number: 5,389,251

[45] Date of Patent: Feb. 14, 1995

[54] ORGANIC CONTAMINANT SEPARATOR

[75] Inventor: Peter Del Mar, Los Alamos, N. Mex.

[73] Assignee: The Regents of the University of California, Oakland, Calif.

[21] Appl. No.: 157,753

[22] Filed: Nov. 23, 1993

Related U.S. Application Data

[60] Division of Ser. No. 912,431, Jul. 13, 1992, Pat. No. 5,273,655, which is a continuation-in-part of Ser. No. 648,774, Jan. 31, 1991, abandoned, which is a division of Ser. No. 418,613, Oct. 10, 1989, Pat. No. 5,037,553.

[51] Int. Cl.⁶ .............................................. B01D 15/08
[52] U.S. Cl. .............................. 210/198.2; 210/502.1
[58] Field of Search ................. 210/635, 656, 198.2, 210/692, 502.1; 95/82, 88; 96/101; 436/161, 162; 422/70

[56] References Cited

U.S. PATENT DOCUMENTS

| | | | |
|---|---|---|---|
| 2,920,478 | 1/1960 | Golay | 55/67 |
| 3,663,263 | 5/1972 | Bodre et al. | 210/198.2 |
| 3,775,309 | 11/1973 | Ito et al. | 210/657 |
| 3,808,125 | 4/1974 | Good | 210/198.2 |
| 3,820,660 | 6/1974 | Halasz et al. | 55/386 |
| 3,822,530 | 7/1974 | Fuller et al. | 55/386 |
| 3,856,669 | 12/1974 | Ito et al. | 210/657 |
| 4,155,846 | 5/1979 | Novak et al. | 210/198.2 |
| 4,207,188 | 6/1980 | Tsuda et al. | 210/198.2 |
| 4,211,658 | 7/1980 | McDonald et al. | 210/198.2 |
| 4,242,227 | 12/1980 | Nestrick et al. | 55/386 |
| 4,276,179 | 6/1981 | Soehngen | 210/679 |
| 4,483,773 | 11/1984 | Yang | 55/386 |
| 4,541,452 | 9/1985 | Paradis | 210/198.2 |
| 4,551,251 | 11/1985 | Kolobow et al. | 210/198.2 |
| 4,591,442 | 5/1986 | Andrews | 210/198.2 |
| 4,672,042 | 6/1987 | Ross | 210/649 |
| 4,808,233 | 2/1989 | Pfannkoch | 210/198.2 |
| 4,826,603 | 5/1989 | Hayes et al. | 210/635 |
| 4,828,996 | 5/1989 | Siegel | 210/635 |
| 4,836,928 | 6/1989 | Aoyagi et al. | 210/635 |
| 4,872,979 | 10/1989 | Golay | 210/635 |
| 5,037,553 | 8/1991 | Del Mar | 210/635 |
| 5,273,655 | 12/1993 | Del Mar | 210/635 |
| 5,308,493 | 5/1994 | Del Mar | 210/635 |

OTHER PUBLICATIONS

Test Methods for Evaluating Solid Wastes, Physical/Chemical Methods SW-846, U.S. Environment Protection Agency Office of Solid Waste and Emergency Response, 3rd Edition, District of Columbia (1987) pp. (Abstract-1), (3510-1-3510-7), (3520-1-3520-7), (8080-1-8080-27).

Mikes Laboratory Handbook of Chromatographic and Allied Method, John Wiley, New York, 1979, pp. 424-425.

Snyder, Introduction to Modern Liquid Chromatography, John Wiley, New York, 1979, pp. 86-88.

Primary Examiner—Ernest G. Therkorn
Attorney, Agent, or Firm—Bruce H. Cottrell; William A. Eklund

[57] ABSTRACT

A process of sample preparation prior to analysis for the concentration of an organic contaminant in an aqueous medium by (a) passing an initial aqueous medium including a minor amount of the organic contaminant through a composite tube comprised of a blend of a polyolefin and a polyester, the composite tube having an internal diameter of from about 0.1 to about 2.0 millimeters and being of sufficient length to permit the organic contaminant to adhere to the composite tube, (b) passing a solvent through the composite tube, said solvent capable of separating the adhered organic contaminant from the composite tube.

Further, an extraction apparatus for sample preparation prior to analysis for the concentration of an organic contaminant in an aqueous medium, said apparatus including a composite tube comprised of a blend of a polyolefin and a polyester, the composite tube having an internal diameter of from about 0.1 to about 2.0 millimeters and being of sufficient length to permit an organic contaminant contained within an aqueous medium passed therethrough to adhere to the composite tube is disclosed.

7 Claims, 2 Drawing Sheets

ORGANIC CONTAMINANT SEPARATOR

This is a divisional of application Ser. No. 07/912,431, filed Jul. 13, 1992, now U.S. Pat. No. 5,273,655, which is a continuation-in-part of application Ser. No. 648,774, filed Jan. 31, 1991, now abandoned, which is a divisional of Ser. No. 418,613, U.S. Pat. No. 5,037,553, filed Oct. 10, 1989.

FIELD OF THE INVENTION

The present invention relates generally to the field of analytical chemistry and more particularly to a sample preparation apparatus and technique preceding a standard analysis, i.e., gas or liquid chromatography for determining the concentration of organic contaminants in an aqueous sample. This invention is the result of a contract with the Department of Energy (Contract No. W-7405-ENG-36).

BACKGROUND OF THE INVENTION

Organic contaminants, e.g., certain organic compounds, especially including many halogenated organic compounds, polyaromatic hydrocarbons and nitroaromatic hydrocarbons, can find their way into the environment through industrial operations and through the use of pesticides. While many of these compounds have been banned or restricted due to potential health hazards, their presence continues in soil and water samples.

Analysis of water and/or soil samples for halogenated organic compounds has traditionally been conducted by addition of an immiscible solvent, e.g., chloroform, to a water sample whereby the halogenated organic compounds will concentrate in the organic phase, i.e., the immiscible solvent (see Test Methods for Evaluating Solid Wastes, Physical/Chemical Methods, SW-846, U.S. Environmental Protection Agency, Office of Solid Waste and Emergency Response, 3rd edition, Dist. of Columbia (1987) describing an EPA approved method, i.e., method 8080 for Organochlorine Pesticides and PCB's wherein aqueous extractions are conducted by either method 3510—Separatory Funnel Liquid-Liquid Extraction or method 3520—Continuous Liquid-Liquid Extraction, each method requiring large amounts of solvents and considerable time). The solvent phase is then separated from the aqueous phase, the majority of the solvent evaporated off and the halogenated organic compound residue analyzed by standard techniques.

Several repetitions of such an organic phase separation process are generally necessary thereby resulting in the use of a significant volume of solvent. Drawbacks to this traditional organic phase separation process include that it is time-consuming, is often rather imprecise and inaccurate, and presents a further environmental problem by the use and potential for release of chlorinated solvent into the atmosphere as the solvent is removed prior to analysis.

Another analytical technique referred to as solid phase extraction has also been used for separation of organic compounds from aqueous samples. This method uses silica particles coated with selected organic molecules, e.g., polyalkylenimino alkyl polyalkoxy silanes or carboalkoxyalkyl silanes, such silica particles often referred to as bonded phase silicas. The coated silica particles are packed into a chromatographic column and a water sample is percolated through the packed column. Organic compounds within the water sample are attracted to the surface coating on the silica and thus be separated from the water. The organic compounds can then be separated from the packed bed by flushing with a small amount of solvent. This method uses significantly less solvent than the traditional method. However, drawbacks of solid phase extraction include: the potential for decomposition of the coating on the silica particles under certain conditions, e.g., under wide pH fluctuations; the tendency for clogging of the packed columns due to the small particle size; the tendency of the coated silica particles to adsorb water which must be subsequently removed; and, the potential for interference during subsequent analysis of a water sample due to compounds added to the coated silica particles during their manufacturing process. Thus, techniques other than traditional organic phase separation or solid phase separation are still desirable for sample preparation prior to the analysis of water samples.

It has been known that many organic compounds, especially halogenated organic compounds, are attracted to polyolefin material such as polyethylene and polypropylene. For example, U.S. Pat. No. 4,276,179 discloses removal of halogenated hydrocarbons from aqueous solutions by contact with microporous polyolefinic absorbents. However, there is no disclosure regarding removal of the halogenated hydrocarbons from the microporous polyolefinic absorbents or determination of halogenated hydrocarbon concentrations in the initial aqueous sample.

One object of this invention to provide an apparatus and process for sample preparation prior to a standard analysis for organic contaminants, e.g., halogen-containing hydrocarbons, polyaromatic hydrocarbons and nitroaromatic hydrocarbons, in a water sample.

A further object of this invention to provide an apparatus and process for sample preparation prior to a standard analysis for organic contaminants, e.g., halogen-containing hydrocarbons, polyaromatic hydrocarbons and nitroaromatic hydrocarbons, in a water sample wherein the sample preparation does not require substantial quantities of solvent in separating the organic contaminants.

Yet another object of this invention to provide an apparatus for sample preparation prior to a standard analysis for organic contaminants, e.g., halogen-containing hydrocarbons, polyaromatic hydrocarbons and nitroaromatic hydrocarbons, in a water sample wherein the apparatus is substantially free of clogging problems and does not undergo the retention of water.

A still further object of this invention to provide an apparatus and process for sample preparation prior to a standard analysis for organic contaminants, e.g., halogen-containing hydrocarbons, polyaromatic hydrocarbons and nitroaromatic hydrocarbons, in a water sample wherein the sample preparation provides cleaner extracts in a quicker process and the apparatus can be reused rather than discarded as are the presently available solid phase extraction materials.

SUMMARY OF THE INVENTION

To achieve the foregoing and other objects, and in accordance with the purposes of the present invention, as embodied and broadly described herein, the present invention provides a process of sample preparation prior to analysis for the concentration of an organic contaminant in an aqueous medium comprising: passing an initial aqueous medium including a minor amount of the organic contaminant through a composite tube comprised of a blend of a polyolefin and a polyester, the composite tube having an internal diameter of from about 0.1 to about 2.0 millimeters and being of sufficient length to permit the organic contaminant to adhere to the composite tube; and, passing a solvent through the composite tube, said solvent capable of removing the adhered organic contaminant from the composite tube.

The present invention further provides an extraction apparatus for sample preparation prior to analysis for the concentration of an organic contaminant in an aqueous medium comprising: a composite tube comprised of a blend of a polyolefin and a polyester, the composite tube having an internal diameter of from about 0.1 to about 2.0 millimeters and being of sufficient length to permit an organic contaminant contained within an aqueous medium passed therethrough to adhere to the composite tube; and, a means of passing through said composite tube both a first predetermined amount of an aqueous medium containing an organic contaminant at a predetermined rate and a second predetermined amount of a solvent capable of separating the adhered organic contaminant from said composite tube.

DETAILED DESCRIPTION

Figure 1A:
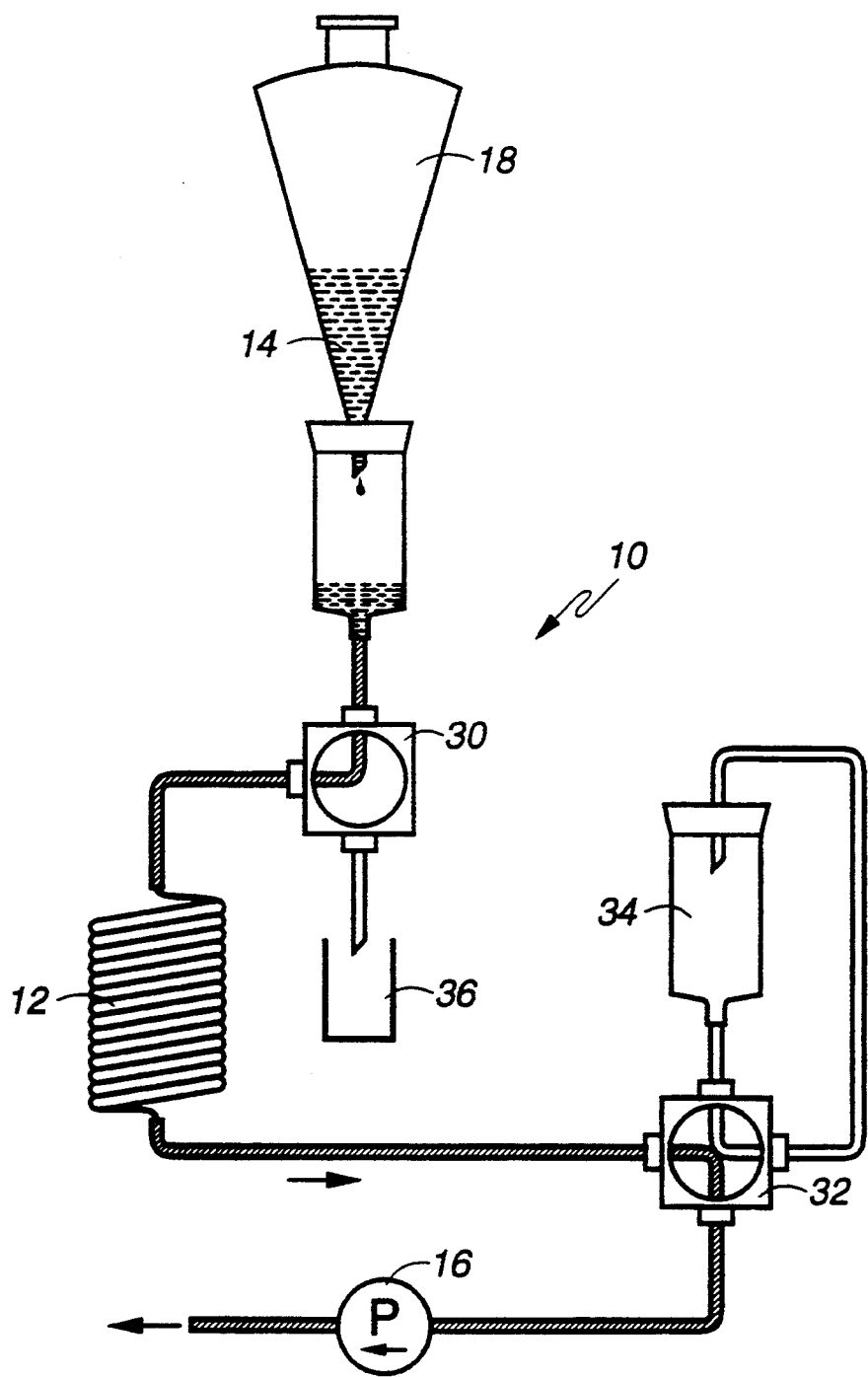
FIG. 1(a) is a schematic drawing of the extraction apparatus of the present invention during the separation stage.

The present invention concerns an extraction apparatus for and a process of sample preparation prior to measuring or determining the concentration of organic contaminants, e.g., aliphatic hydrocarbons, halogen-containing hydrocarbons, substituted aromatic hydrocarbons, polyaromatic hydrocarbons, ethers or amines, especially halogen-containing hydrocarbons, polyaromatic hydrocarbons or nitroaromatic hydrocarbons, in an aqueous medium. It has now been found that certain organic contaminants can be separated from an aqueous medium by passing the aqueous medium through a composite column or tube comprised of a blend of a polyolefin and a polyester, the composite tube having a sufficient diameter and length so that organic contaminants can be separated from the aqueous medium by adhering to the composite tube material. Subsequently, the organic contaminants can be removed or separated from the composite tube or column by passing a solvent through the composite tube whereby the concentration of the organic contaminants in the initial aqueous medium can be readily determined.

It is the high affinity of the composite tube materials for the various organic contaminants and the ability to subsequently separate the organic contaminants from the composite tube materials, i.e., the polyolefin or polyfluorocarbon materials as well as the carbon allotrope materials, that facilitates the present process and apparatus for measurement of the organic contaminant concentrations in the aqueous samples.

The composite tubing can be formed, e.g., by processes generally well known to those skilled in the polymer arts, such as by coextrusion of the materials.

Suitable polyolefinic materials may include polyethylene, polypropylene, poly-3-methyl butene-1, poly-4-methyl pentene-1, as well as copolymers of propylene, 3-methyl butene-1, 4-methyl pentene-1, or ethylene with each other or minor amounts of other olefins, e.g., copolymers of propylene and ethylene, copolymers of a major amount of 3-methyl butene-1 and a minor amount or a straight chain alkene such as n-octene-1, n-hexadecene-1, n-octadecene-1 or other similar long chain alkenes as well as copolymers of 3-methyl pentene-1 and any of the previously mentioned straight chain alkenes. The preferred polyolefins are polyethylene and polypropylene with polyethylene being most preferred.

Preferably, the polyolefin tubing should not contain additives that interfere with the subsequent analysis for the organic contaminants. Polyolefin tubing can typically include various plasticizers, flexibilizers, anti-oxidants, anti-static agents and the like for use in other applications. Selection of a polyolefin tubing with a minimum of additives simplifies the subsequent analysis. Suitable polyester materials for blending with the polyolefin include, e.g., polyethylene terephthalate.

The composite blend of the polyolefin and the polyester can generally include any ratio of the two individual polymer materials suitable for extraction of the organic contaminant. While not wishing to be bound by the present explanation, more of the polar polyester material is believed to be better for the extraction of polar organic contaminants. Usually, the composite blend contains a major portion of the polyolefin and a minor portion of the polyester, generally from about 51 to about 99 percent by weight of the polyolefin, the remainder polyester, preferably from about 75 to about 95 percent by weight polyolefin, the remainder polyester, and more preferably from about 80 to about 90 percent by weight polyolefin, the remainder polyester.

The composite column or tube, through which the organic contaminant-containing water sample is passed, should have its internal diameter minimized to increase the contact between the water sample and the composite tube walls. The lower limit for the internal diameter is limited only by the ability to form such a tube or column and by a need to avoid plugging of the composite tube or column by any particulates in the water sample. Generally, the internal diameter of the composite tube will be from about 0.1 to about 2.0 millimeters, preferably from about 1.0 to about 2.0 millimeters, more preferably from about 1.4 to about 1.8 millimeters. The composite tube or column in the present invention is devoid of any packing material as such packing material presents the potential for clogging. The use of unfilled tubing alleviates any possible clogging so long as the internal diameter of the composite tubing is greater than any particles in the aqueous medium.

The length of the composite column or tube should be of sufficient length to permit organic contaminants in the initial water sample to contact and adhere to the inner wall of the composite tubing. Generally, with water samples of about 100 to about 500 milliliters (ml) in size and typical organic contaminant concentrations of from about 0.01 to about 10.0 or more micrograms per liter, composite tube lengths of from about 5 feet to about 100 feet are sufficient, preferably from about 10 feet to about 50 feet. Variations in tube length can easily be adjusted for different sample sizes, concentrations and internal tubing diameters.

The water sample can be contacted with the composite tube at any convenient temperature, e.g., from about 10° Centigrade (C.) to about 50° C., or pressure, e.g., superatmospheric, subatmospheric or atmospheric.

Higher temperatures are not generally preferred as the solubilities of the organic contaminants in the aqueous samples can be affected. The most convenient temperature is generally ambient temperature and the most convenient pressure is generally atmospheric.

After the water sample is passed through the composite column or tube to separate organic contaminants from the water, a suitable solvent can be passed through the composite column or tube to separate the adhered organic contaminants from the composite tube. Typically, as little as 10 ml of solvent is needed flush or separate the organic contaminants from the composite tubing. This is substantially less solvent than necessary in previous analytical techniques for such organic contaminants and is one of the major advantages of the present process and apparatus. Suitable solvents include hexane, iso-octane, acetone, acetonitrile, and lower alcohols, e.g., methanol, ethanol, propanol and butanol. Preferred solvents include hexane and iso-octane.

In the process of the present invention, the water sample is passed through the composite column or tube at flow rates of from about 0.6 to about 2.0 ml/minute, preferably from about 0.8 to about 1.2 ml/minute. The water sample may be passed through the composite tube by gravity flow but the flow rate is preferably controlled by a pump, e.g., a peristaltic pump.

Figure 1B:
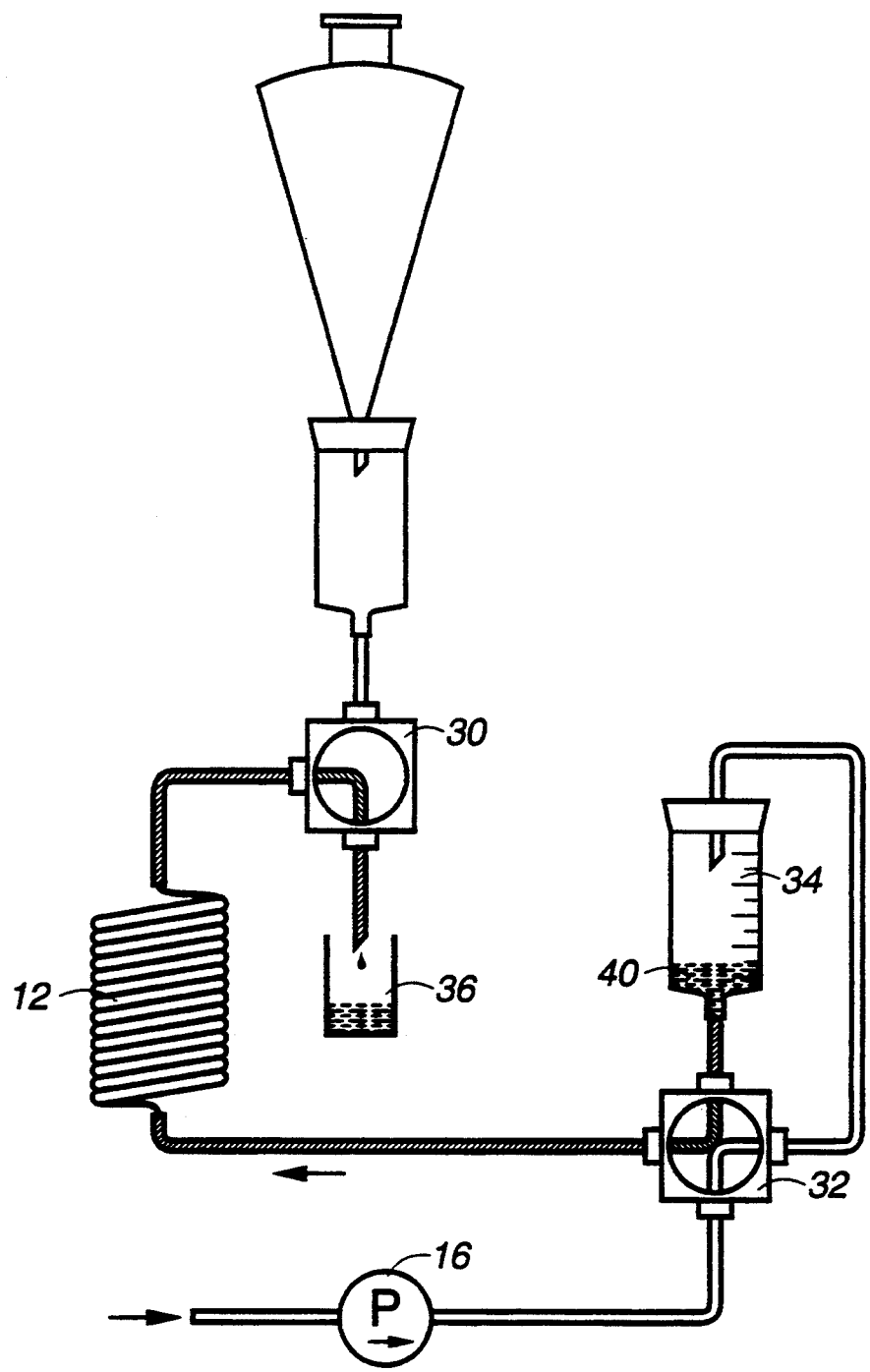
FIG. 1(b) a schematic drawing of the extraction apparatus of the present invention during the removal or elution stage.

FIGS. 1(a) and 1(b) show schematic drawings of the extraction apparatus used for sample preparation of an aqueous medium containing an organic contaminant, FIG. 1(a) in the separation stage and FIG. 1(b) in the removal or elution stage. Apparatus 10 includes as a principal component a composite tube 12 having an internal diameter of from about 0.1 to about 2.0 millimeters and tube 12 being of sufficient length to permit an organic contaminant contained within an aqueous sample 14 passed therethrough to adhere to the composite tube. The apparatus further includes a means of passing a predetermined amount of aqueous sample 14 containing an organic contaminant through tube 12. at a predetermined rate, and of passing a predetermined amount of a solvent 40 capable of removing or separating the adhered organic contaminant from composite tube 12 through the tube.

The means of passing a predetermined amount of an aqueous medium containing an organic contaminant through the composite tube at a predetermined rate can include a pump 16 attached to an outflow end of the composite tube whereby the flow rate of the aqueous medium through the composite tube can be controlled. Optionally, the apparatus may further include a holding vessel 18 wherein the aqueous medium is held prior to processing.

The means of passing a predetermined amount of solvent 40 through composite tube 12 can include a second holding vessel 34 wherein solvent 40 is held prior to the flushing of the composite tube. Alternatively, solvent 40 can be entered into composite tube 12 from the same holding vessel as the initial aqueous medium 14 as long as proper rinsing precautions are taken to avoid inadvertent contamination of the solvent.

Apparatus 10 can further include a means of collecting said predetermined amount of solvent after passage through said composite tube. Such collection means can be a vessel 36 of sufficient size to contain the flushed solvent.

Apparatus 10 can still further include a first valve means 30 and a second valve means 32 whereby the flow of the liquids through apparatus 10 is controlled.

Calculation of the concentration of organic contaminants in the predetermined amount of aqueous medium can be accomplished by first concentrating the final solvent elute containing the organic contaminants removed from the aqueous sample by evaporating off most of the solvent and then injecting the organic contaminant-containing solvent into a gas chromatograph equipped with a suitable detector such as an electron capture detector or a flame ionization detector. Such techniques are well known to those skilled in the art of analytical chemistry.

The organic contaminants which may be removed from aqueous media include halogen-containing hydrocarbons such as aliphatic, cycloaliphatic, and heterocyclic halogen-containing hydrocarbons containing from about 1 to about 30 carbon atoms, aromatic halogen-containing hydrocarbons and their derivatives such as alkyl-substituted aromatic halogen-containing hydrocarbons having from about 6 to about 30 carbon atoms. Many such aromatic halogen-containing hydrocarbons are typically employed as pesticides. Generally, the halogen-containing hydrocarbons include one or more chlorine or bromine atoms.

Representative examples of chlorine-containing hydrocarbons include N-(trichloromethylthio) phthalimide (Phalton fungicide);
1,2,3,3,10,10-hexachloro-1,4,4a, 5,8,8a-hexahydro-1,4,5,8-endo-dimethanonaphthalene (aldrin);
1,2,3,4,10,10-hexachloro-6,7-epoxy-1,4,4a, 5,6,7,8,8a-octahydro-1,4-endo-exo-5,8-dimethanonaphthalene (diendrin);
1,2,3,4,10,10-hexachloro-6,7-epoxy-1,4,4a, 5,6,7,8,8a-octahydro- 1,4-endo-endo-5,8-dimethanonaphthalene (endrin);
dichlorodiphenyldichloroethylene (DDE);
dichlorodiphenyldichloro-ethane (DDD);
1,1,1-trichloro-2,2-bis (chlorophenyl)ethane (DDT);
1,4,5,6,7,8,8-heptachloro-3a,4,7,7a-tetrahydro-4,7-methanoindene (heptachlor);
octachloro-4,7-methanotetrahydroindane (chlordane);
N-trichloromethylthio- or N-tetrachloromethylthio-substituted (haloalkyl sulfenylated) carboximides such as cis-N-(trichloromethylthio)-4-cyclohexene-1,2-dicarboximide (Captan TM );
N-(1,1,2,2-tetrachloroethylthio)-4-cyclohexene-1,2-dicarboximide (Difolatan TM fungicide);
gamma-benzene hexachloride (lindane);
toxaphene;
methoxychlor;
hexachlorocyclopentadiene;
carbon tetrachloride;
trichloroethylene;
trichloromethane;
ethylene dichloride;
and vinyl chloride.

Other representative examples of halogen-containing hydrocarbons and their derivatives include polychlorinated biphenyls, such as the Arochlor TM series of compounds made by Monsanto Co. Specific common chlorobiphenyl compounds include 2-chlorobiphenyl; 3-chlorobiphenyl; 4-chlorobiphenyl; 2,2'-dichlorobiphenyl; 3,3'-dichlorobiphenyl; 4,4'-dichlorobiphenyl; 5-dichlorobiphenyl; 2,5-dichlorobiphenyl; 3,4-dichlorobiphenyl; 2,3-dichlorobiphenyl; 2,4'-dichlorobiphenyl; 2,4,5-trichlorobiphenyl; 2,3,5-trichlorobiphenyl; 2,4,4'-trichlorobiphenyl; 2,5,4'-trichlorobiphenyl; 3,5,4'-trichlorobiphenyl; 3,4,2'-trichlorobiphenyl; 3,5,2'-trichlorobiphenyl; 3,4,3',4'-tetrachlorobiphenyl; 3,4,2',5'-tetrachlorobiphenyl; 2,6,2',6'-tetrachlorobiphenyl; 2,5,3',5'-tetrachlorobiphenyl; 2,4,2',4'-tetrachlorobiphenyl; 2,5,2',5'-tetrachlorobiphenyl; 2,4,5,3',4'-pentachlorobiphenyl; 3,4,5,3',4',5,-hexachlorobiphenyl; 2,4,6,2',4',6'-hexachlorobiphenyl; 2,3,5,6,2',3',5',6'-octachlorobiphenyl; and 2,3,4,5,6,2',3',4',5',6'-decachlorobiphenyl.

Still other representative examples of organic contaminants include nitroaromatic hydrocarbons such as 2,4-dinitrotoluene, 2,6-dinitrotoluene, nitrobenzene, and 4,6-dinitro-2-methylphenol.

Still other representative examples of organic contaminants include phenol compounds such as phenol, 2-chlorophenol, 2-nitrophenol, 4-nitrophenol, 2,4-dinitrophenol, 2,4-dimethylphenol, 2,4-dichlorophenol, 4-chloro-3-methylphenol, 2,4,6-trichlorophenol, 4,6-dinitro-2-methylphenol and pentachlorophenol. Some of the above listed compounds are found on a EPA semi-volatile organic analysis list commonly referred to as the SVOA's. Still other representative examples of organic contaminants found on the SVOA list are N-nitrosodimethylamine, N-nitroso-di-n-propylamine, n-nitrosodiphenylamine, bis(2-chloroethyl)ether, bis(2-chloroisopropyl)ether, 4-chlorophenylphenyl ether, 4-bromophenylphenyl ether, 1,2-dichlorobenzene, 1,3-dichlorobenzene, 1,4-dichlorobenzene, 1,2,4-trichlorobenzene, hexachlorobenzene, bis(2-chloroethoxy)methane, hexachloroethane, isophorone, hexachlorobutadiene, dimethyl phthalate, diethyl phthalate, di-n-butyl phthalate, butyl benzyl phthalate, bis(2-ethylhexyl)phthalate, di-n-octyl phthalate, benzidine, 3,3'-dichlorobenzidene, p-chloro-m-cresol, 4,6-dinitro-o-cresol, 1,2-diphenyl hydrazine, phenanthrene, 2-chloronaphthalene, acenaphthylene, acenaphthene, chrysene, fluorene, benzo(a)anthracene, dibenzo(a,h)anthracene, fluoroanthene, benzo(b)fluoroanthene, benzo(k)fluoroanthene, pyrene, benzo(a)pyrene, indeno (1,2,3-cd)pyrene, and benzo(ghi)perylene.

Polyaromatic hydrocarbons may also be separated from aqueous samples by the present process and apparatus. Among the polyaromatic hydrocarbons which may be separated are included naphthalene, substituted naphthalenes, anthracene, substituted anthracenes and the like.

The present invention is more particularly described in the following example which is intended as illustrative only, since numerous modifications and variations will be apparent to those skilled in the art.

EXAMPLE 1

Sample aliquots of water were each spiked with an equal portion of a known organic contaminant sample. For comparison, separate sample preparation apparatuses were used, a first apparatus including a ten foot column of polyethylene tubing having an internal diameter of 1 millimeters(mm) and additional apparatuses including a ten foot column of a composite tubing having a blend of 90, 95, and 97 percent by weight polyethylene respectively and the remainder polyethylene terephthalate, the tubing having an internal diameter of 1 mm. Each apparatus included a pump at a setting sufficient to pump the liquid sample through the tubing at a flow rate of about 1.0 ml/min. Spiked water samples were pumped through the tubing of each apparatus. After each water sample was passed through the tubing, about 10 ml of hexane was passed through the tubing at a rate of about 1.0 ml/min. A few particles of sodium sulfate were placed within the collection vessel to scavenge any residual water. The solvent (hexane) extract was evaporated down to a one ml volume under dry nitrogen, spiked with 40.0 microliters of an internal standard mix containing four brominated biphenyls in iso-octane, and analyzed in a HP-5880 gas chromatograph (available from the Hewlett-Packard Co.) with an electron capture detector. The time for completion of each sample was about three hours.

The recovery results of the sample runs analyzed by the gas chromatograph are shown in Table 1.

TABLE 1

| organic contaminant | recovery of organic contaminant from solution (percentage) | | | |
|---|---|---|---|---|
| | 100% PE tubing | 97% PE/3% PET tubing | 95% PE/5% PET tubing | 90% PE/10% PET tubing |
| lindane | 11% | — | 16% | — |
| 2,4-dinitrotoluene | 1.5% | 2.3% | 3.2% | 4.2% |

A comparison of the values obtained in Example 1 with polyethylene tubing versus the composite tubing of polyethylene and polyethylene terephthalate shows the increased recoveries possible with the composite tubing. Such improved recoveries can augment the accuracy and precision obtained with the present apparatus and process wherein the composite tube is employed. Additionally, the present apparatus and process use significantly less solvent than either the present separatory funnel liquid-liquid extraction process or continuous liquid-liquid extraction process. Also, the present apparatus and process allows sample preparation to be completed in substantially less time and with substantially less solvent than the present EPA approved separatory funnel liquid-liquid extraction.

Although the present invention has been described with reference to specific details, it is not intended that such details should be regarded as limitations upon the scope of the invention, except as and to the extent that they are included in the accompanying claims.

What is claimed is:

1. An extraction apparatus for sample preparation prior to analysis for the concentration of an organic contaminant in an aqueous medium comprising:

a. a composite tube comprised of a blend of a polyolefin and a polyester, the composite tube having an internal diameter of from about 0.1 to about 2.0 millimeters and being of sufficient length to permit an organic contaminant contained within an aqueous medium passed therethrough to adhere to the composite tube; and b. a means of passing through the composite tube both a first predetermined amount of an aqueous medium containing an organic contaminant at a predetermined rate whereby the organic contaminant adheres to the composite tube and a second predetermined amount of a solvent capable of removing the adhered organic contaminant from said composite tube.

2. The apparatus of claim 1 wherein the polyolefin is comprised of polyethylene or polypropylene.

3. The apparatus of claim 1 wherein the polyester is polyethylene terephthalate.

4. The apparatus of claim 1 wherein the polymer blend includes a major portion of the polyolefin and a minor portion of the polyester.

5. The apparatus of claim 1 wherein the polymer blend includes from about 51 to about 99 percent by weight of the polyolefin and the remainder polyester.

6. The apparatus of claim 1 wherein the internal diameter of the composite tube is from about 0.3 to about 1.0 millimeter.

7. The apparatus of claim 1 further including a collection means for collecting the solvent after passage through the composite tube.

* * * * *